United States Patent [19]

Matolcsy et al.

[11] Patent Number: 4,843,177
[45] Date of Patent: Jun. 27, 1989

[54] SUBSTITUTED ACETAMIDE DERIVATIVES WITH AN ANTIDOTE ACTION, ANTIDOTE COMPOSITIONS CONTAINING SUCH COMPOUNDS, SELECTIVE HERBICIDE COMPOSITIONS CONTAINING THESE ANTIDOTES AND A PROCESS FOR THE PREPARATION OF SUBSTITUTED ACETAMIDE DERIVATIVES

[75] Inventors: Gyorgy Matolcsy; Barna Bordas; Antal Gimesi; Magdolna Kovacs; Marton Tüske, all of Budapest, Hungary

[73] Assignee: Eszakmagyaroszagi Vegyimuvek, Sajobabony, Hungary

[21] Appl. No.: 838,271

[22] Filed: Mar. 10, 1986

Related U.S. Application Data

[63] Continuation of Ser. No. 513,215, Jul. 13, 1983, Pat. No. 4,605,764.

[30] Foreign Application Priority Data

Jul. 14, 1982 [HU] Hungary ............................ 2288/82

[51] Int. Cl.⁴ ................ C07C 103/127; C07C 103/34; A01N 37/18
[52] U.S. Cl. ................... 564/209; 569/214; 71/118
[58] Field of Search ........................ 569/209; 564/214; 71/118

[56] References Cited

U.S. PATENT DOCUMENTS 4,021,224  5/1977  Pallos et al. ............. 564/209 X
4,330,323  5/1982  Gorny et al. ............. 564/209 X
4,443,628  4/1986  Ringhart .................. 564/209

Primary Examiner—Paul F. Shaver
Attorney, Agent, or Firm—Herbert Dubno; Jonathan Myers

[57] ABSTRACT

The invention relates to acetamides of the formula (III),

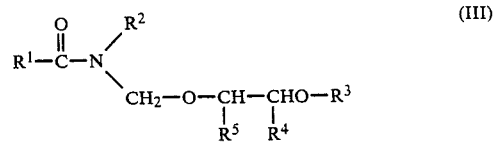

wherein
R¹ stands for a halogenated alkyl group containing 1 to 2 carbon atoms, preferably for a dichloro- or dibromoalkyl group;
R² stands for a straight or branched alkyl group containing 1 to 6 carbon atoms or an alkenyl group containing 2 to 6, preferably 3, carbon atoms;
R³ stands for an alkyl group containing 1 to 6, preferably 1 to 4, carbon atoms, an alkoxyalkyl group of altogether 2 to 6, suitably 4 carbon atoms, or a phenyl group;
R³ and R⁴ together may stand for a propylene or butylene group;
R⁴ and R⁵ stand independently from each other for hydrogen or a methyl group; and
R⁴ and R⁵ together may stand for a propylene or butylene group.

These compounds are antidotes and can be used along or together with herbicidal agents. The invention comprises such compositions and a process for the preparation of said compounds.

10 Claims, No Drawings

SUBSTITUTED ACETAMIDE DERIVATIVES WITH AN ANTIDOTE ACTION, ANTIDOTE COMPOSITIONS CONTAINING SUCH COMPOUNDS, SELECTIVE HERBICIDE COMPOSITIONS CONTAINING THESE ANTIDOTES AND A PROCESS FOR THE PREPARATION OF SUBSTITUTED ACETAMIDE DERIVATIVES

CROSS REFERENCE TO RELATED APPLICATION

This application is a continuation of Ser. No. 513,215, filed July 13, 1983, now U.S. Pat. No. 4,605,764.

FIELD OF THE INVENTION

This invention relates to substituted acetamide derivatives of the formula

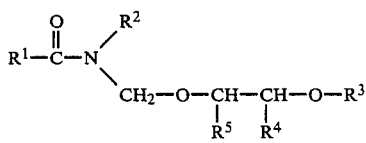

with an antidote action, to antidote compositions containing such compounds, and to selective herbicide compositions containing these antidotes together with the herbicidally active compounds, preferably thiocarbamates of the formula

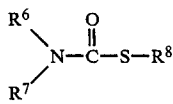

or the chloroacetanilides of the formula

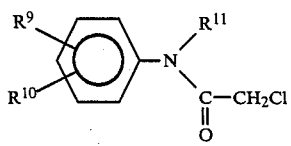

The invention further relates to the preparation of antidote compositions containing the compounds of the formula (III) as active ingredient as well as to the synthesis of the compounds of the formula (III) comprising the reaction of N-chloromethyl compounds of the formula

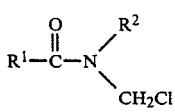

with alcohols of the formula (V).

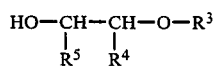

In the formula (I)
$R^6$ and $R^7$ can be alkyl containing 1 to 4 carbon atoms or cyclohexyl; or
$R^6$ and $R^7$ together represent a hexamethylene group; and
$R^8$ is alkyl containing 1 to 3 carbon atoms.

In the formula (II)
$R^9$ and $R^{10}$ are hydrogen or alkyl containing 1 to 3 carbon atoms; and
$R^{11}$ is alkyl containing 1 to 4 carbon atoms or an alkoxyalkyl group containing not more than 4 carbons.

In the formula (III)
$R^1$ is haloalkyl containing 1 to 2 carbon atoms, preferably a dichloro- or dibromoalkyl;
$R^2$ is straight or branched alkyl containing 1 to 6 carbon atoms or alkenyl containing 2 to 6, preferably 3 carbon atoms;
$R^3$ is alkyl group containing 1 to 6, preferably 1 to 4, carbon atoms, alkoxyalkyl with a total of 2 to 6, preferably 4 carbon atoms, or phenyl;
$R^3$ and $R^4$ together represent a propylene or butylene group;
$R^4$ and $R^5$ are independent and can be hydrogen or methyl; or
$R^4$ and $R^5$ together represent a propylene or butylene group.

BACKGROUND OF THE INVENTION

One of the most important requirements in the case of herbicide compositions is the selectivity, that is, the composition has to kill effectively the weeds when used for cultivated plants, while it should exert at most a minimum effect on the development of the cultivated plants. A number of herbicides are known which, in addition to the control of weeds, possess substantial damaging effect on the cultivated plants. Such herbicides are thiocarbamate and chloroacetanilide derivatives.

Thiocarbamate derivatives and herbicide compositions containing these compounds are disclosed in the U.S. Pat. Nos. 2,913,327 and 3,175,897. Of these, S-ethyl-N,N-di-(n-propyl)thiocarbamate (EPTC) and S-ethyl-N-N-diisobutylthiocarbamate (butylate) are widely used in agricultural practice. Chloroacetanilide derivatives are described for instance in the U.S. Pat. Nos. 3,442,945 and 3,547,620. Outstanding representatives of proved value in this group are, for example, 2-methyl-6-ethyl-N-(ethoxymethyl)chloroacetanilide (acetochlor), 2-methyl-6-ethyl-N-(1-methyl-2-methoxyethyl-chloroacetanilide (metholachlor) and 2,6-diethyl-N-(methoxymethyl) chloroacetanilide (alachlor).

Compositions comprising the aforementioned thiocarbamate and chloroacetanilide type active agents possess an excellent herbicidal activity, but also exert a harmful effect on cultivated plants, for example, on maize and other cereals.

In order to reduce or prevent the effect damaging the cultivated plants and to enhance the selectivity, a compound antagonizing this harmful effect, the so-called antidote, is mixed with the herbicidal agent or composition, or the herbicide composition is used together with a composition containing an antidote for obtaining the same herbicidal activity without any damage to the cultivated plants.

Antidotes that can be used against the effect damaging cultivated plants and particularly the maize of herbicidal compositions containing thiocarbamates are disclosed for instance in the Belgian patent specification Nos. 782,120 and 806,038; in the U.S. Pat. Nos. 3,893,838 and 3,931,313; in the British patent specification Nos. 1,420,685 and 1,512,540; as well as in the Hungarian patent specification Nos. 176,784, 165,736 and 168,977.

Of these antidotes, N,N-diallyldichloroacetamide, described in the Hungarian patent specification No. 165,736, is generally used in agricultural practice. In addition to this most widely used antidote, the antiphytotoxic (that is phytotoxicity reducing) features of various dichloroacetamide derivatives have been studied in detail.

In one of these papers [Res. Discl. 143, 8 (1976)] the property of reducing the harmful effect of thiocarbamates of a group of heterocyclic compounds containing nitrogen were investigated and it was stated that no damaging effect was observed when for example a combination of N-dichloroacetylhexamethyleneimine with S-trichloroallyl N,N-diisopropylthiocarbamate (triallate) was used in a 16:1 to 1:4 ratio.

Similarly, the action of dichloroacetamide derivatives has been disclosed in two other papers [J. Agric. Food. Chem. 26, 1,137–40 (1978); and ibid 27, 3, 543–7 (1979)] reporting on the synthesis of dichloroacetamide derivatives and trying to find correlations between the molecular structure of the dichloroacetamide antidotes and thiocarbamates on the basis of analogy.

OBJECT OF THE INVENTION

In spite of the results achieved in the development of antidotes a continuous demand exists for increasing their efficiency, selectivity and spectrum of activity as well as on extending their assortment by new compounds that are easy to prepare from available raw materials on an industrial scale, in an economical route and by the means of a relatively simple process technology.

DESCRIPTION OF THE INVENTION

It was observed during our experiments that the new acetamide derivatives of the formula (III) and the compositions containing them are useful to enhance mainly the selectivity of thiocarbamate and chloroacetanilide derivatives and of the herbicide compositions containing them, that is, to reduce or to prevent their effect damaging the development of cultivated plants without any decrease in the herbicidal activity.

The substituted acetamide derivatives of the formula (III) of the invention are prepared by reacting an N-chloromethyl compound of the formula (IV) with an alcohol of the formula (V).

In the formula (III) $R^1$ can be a halogenated alkyl group containing 1 to 2 carbon atoms, the halogen is mainly chlorine or bromine; the ethyl group may contain the halogens on the same or on different carbon atoms, while preferably $R^1$ means a dichloromethyl or 1,2-dibromoethyl group $R^2$ is a straight or branched alkyl group of 1 or 6 carbon atoms and an alkenyl group of 2 to 6 carbon atoms, suitably of 3 carbons, while preferably $R^2$ means methyl, ethyl, n-propyl, isopropyl, n-butyl, isobutyl, sec-butyl, n-pentyl or allyl; $R^3$ means an alkyl group of 1 or 6 carbon atoms, suitably of 1 to 4 carbon atoms, and an alkoxyalkyl group of altogether 2 to 6 carbon atoms, mainly of 4 carbon atoms, or a phenyl group, while preferably $R^3$ means methyl, ethyl, n-propyl, isopropyl, n-butyl, isobutyl, sec-butyl, methoxyethyl, ethoxyethyl or phenyl; $R^3$ and $R^4$ together may also mean a propylene or butylene group; $R^4$ and $R^5$ mean independently from each other hydrogen or methyl, while $R^4$ and $R^5$ together may mean a propylene or butylene group.

In the formula (IV) $R^1$ and $R^2$ are as defined above.

In the formula (V) $R^3$, $R^4$ and $R^5$ are as defined above.

The N-chloromethyl compound of the formula (IV) is reacted with the alcohol of the formula (V) in a solvent, optionally in the presence of an acid binding agent. Under the conditions of this reaction inert solvents are useful such as benzene, toluene, xylene, chlorobenzene, dichloromethane, dichloroethane, carbon tetrachloride and chloroform; however an excess of the alcohol of the formula (V) may also serve as solvent.

Any of the generally used acid binding agents can be employed for binding the hydrochloric acid formed, such as alkali metal carbonates and alkali metal hydrogencarbonates; organic amines, for example trialkylamines and pyridine; or, the alkoxides formed from the alchohol of the formula (V) with an alkali metal.

The use of an acid binding agent can be avoided when during the reaction an inert gas, such as dry air or nitrogen, is led through the mixture under heating, in order to remove the hydrochloric acid formed.

In general, molar equivalents of the starting materials of the formulae (IV) and (V) are reacted; however, it is suitable to use a slight excess of the compound of the formula (V); an even larger excess is used when it plays the role of a solvent.

The temperature of this reaction ranges from 0° C. to the boiling point of the solvent used and preferably is between 15° and 55° C., but it is of advantage to work at room temperature or slightly above. Cooling may also be employed in the view of the exothermicity of the reaction. After the reaction is over, the mixture is worked up in a known manner. If desired, the product obtained may be purified in a way known per se. The crude product prepared by the process of the invention is useful for plant protection without further purification.

The N-chloromethyl compounds of the formula (IV) used as starting materials can be prepared by means of a process analogous to that disclosed in the Belgian patent specification No. 621,378, by reacting an appropriate carboxylic acid chloride with an N,N,N-trisubstituted hexahydrotriazine in an inert solvent. The N,N,N-trisubstituted hexahydrotriazine can, in turn, easily be synthetized with a good yield by a method known from the literature, that is, by reacting the appropriate primary amine with aqueous formaldehyde solution (Smolin, E.M. and Rapoport, L.: The Chemistry of Heterocyclic Compounds: S-triazines and Derivatives, pp. 476–489, Interscience Publishers Inc., New York, 1959).

A part of the alcohols of the formula (V) are well-known, cheap solvents generally used in the practice (2-methoxyethanol, 2-ethoxyethanol, 2-butoxyethanol and the like); another part of those are generally used for other industrial purposes (tetrahydrofurfuryl alcohol, 2-phenoxyethanol); or, they can be prepared by known methods such as 1-methoxy-2-propanol, 2-methoxy-1-propanol [J. Am. Chem. Soc. 72, 1251 (1950)] and 2-methoxycyclohexanol-[J. Am. Chem. Soc. 65, 2196 (1943)].

SPECIFIC EXAMPLES

The preparation of the compounds of the formula (III) is illustrated by the following non-limiting Examples.

Example 1

Preparation of N-allyl-N-(2-methoxyethoxymethyl)-dichloroacetamide

A solution of N-allyl-N-chloromethyldichloroacetamide (21.7 g., 0.1 mole) and 2-methoxyethanol (8.4 g., 8.7 ml., 0.11 mole) in dry chloroform (50 ml.) is placed in a round-bottomed, four-necked flask of 250 ml, equipped with a calcium chloride tube, reflux condenser, mechanical stirrer, dropping funnel and thermometer. Triethylamine (10.1g., 13.9 ml., 0.1 mole) is added under stirring and external cooling in such a rate that the temperature does not exceed 35° C. After the addition is complete, the mixture is stirred for an additional 2 hours at room temperature. The mixture is washed with water (2×70 ml) for removing the triethylamine hydrochloride formed, the chloroform solution is dried over anydrous sodium sulfate and, after distillation of the chloroform, the product is dried under reduced pressure to give 23.6 g. (92%) of a pale yellow oil which is the named compound of 95% purity according to an analysis by gas chromatography; $n_D^{25} = 1.4801$. This product is directly useful for practical purposes.

Example 2

Preparation of N-allyl-N-(ethoxyethoxymethyl) dichloroacetamide

A solution of N-allyl-N-chloromethyldichloroacetamide (43.4g., 0.2 mole) and 2-ethoxyethanol (19.8 g., 21.3 ml., 0.22 mole) in dry chloroform (100 ml) is weighed in a round-bottomed flask of 250 ml, equipped with a reflux condenser, thermometer and with a tube, reaching to the bottom, for air introduction. The end of this tube is connected to a drying tower filled with potassium hydroxide pellets. By applying a slight reduced pressure on the top of the reflux condenser dry air is bubbled through the mixture while maintaining the temperature at 50°–55° C.

The reaction proceeds with a vigorous evolution of gaseous hydrogen chloride. According to gas chromatographic analysis the reaction of the starting chloromethyl derivative is complete within 3 hours. The mixture is washed with sodium carbonate (4 g.), dissolved in water (100 ml.) and then with water (100 ml.), dried over anhydrous sodium sulfate and, after distillation of the chloroform, the product is evaporated to dry under reduced pressure. Thus, 47.0 g (87%) of the named product are obtained as a pale yellow oil; $n_D^{25} = 1.4768$.

Example 3

Preparation of N-propyl-N-(2-ethoxyethoxymethyl)-dichloroacetamide

A solution containing N-propyl-N-chloromethyldichloroacetamide (21.9 g., 0.1 mole) and 2-ethoxyethanol (30 ml.) is weighed in a flask equipped as in Example 1. A solution prepared from metallic sodium (2.3 g., 0.1 mole) with ethoxyethanol (20 ml.) is added to the solution under stirring and cooling by water in such a rate that the temperature of the mixture is maintained below 35° C. After the addition is complete, the mixture is stirred for an additional 2 hours at room temperature. Then, the bulk of ethoxyethanol is removed under reduced pressure and the residue is dissolved in chloroform (80 ml.). The chloroform solution is washed with water (2×100 ml.), dried over anhydrous sodium sulfate and the solvent is distilled under reduced pressure to give 23.2 g. (90.0%) of the named product as an oil; $n_D^{25} = 1.4651$.

Example 4

Preparation of N-isopentyl-N-(2-ethoxyethoxymethyl)dichloroacetamide

The solution of N-isopentyl-N-chloromethyldichloroacetamide (24.7 g., 0.1 mole) and 2-ethoxyethanol (9.9 g., 10.7 ml., 0.11 mole) in dry benzene (70 ml) is weighed in a four-necked, round-bottom flask of 250 ml, equipped with a calcium chloride tube, reflux condenser, mechanical stirrer, dropping funnel and thermometer. Triethylamine (10.1 g., 13.9 ml., 0.1 mole) is added to this solution under stirring and cooling by water in such a rate that the temperature is maintained below 40° C. After the addition is complete, the mixture is stirred for an additional 2 hours at room temperature. The mixture is washed with water (2×100 ml.) to remove triethylamine hydrochloride and the possible hydrophilic side-product, the benzene solution is dried over anhydrous sodium sulfate after distillation of the solvent and the residue is evaporated to dry under reduced pressure to give 27.9 g. (93%) of the named product as a pale yellow oil which is of 96% purity according to analysis by gas chromatography and is directly useful for practical purposes without any purification; $n_D^{25} = 1.4649$.

Table 1 illustrates the compounds of the formula (III) prepared in an analogous way to that described in Examples 1 to 3.

TABLE 1

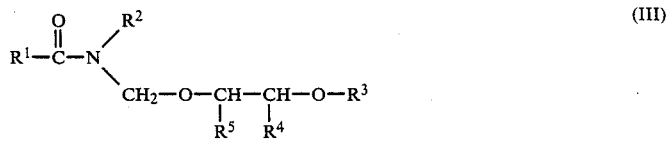

(III)

| Sign of the compound | $R^1$ | $R^2$ | $R^3$ | $R^4$ | $R^5$ | $n_D^{25}$ | Yield (%) |
|---|---|---|---|---|---|---|---|
| A | —CHCl$_2$ | —CH$_2$CH=CH$_2$ | —CH$_3$ | H | H | 1.4801 | 92 |
| B | —CHCl$_2$ | —CH$_2$CH=CH$_2$ | —C$_2$H$_5$ | H | H | 1.4768 | 87 |
| C | —CHCl$_2$ | —CH$_2$CH=CH$_2$ | C$_4$H$_9$ | H | H | 1.4676 | 94 |
| D | —CHCl$_2$ | —CH$_2$CH=CH$_2$ | —CH$_2$CH$_2$OC$_2$H$_5$ | H | H | 1.4661 | 89 |
| E | —CHCl$_2$ | —CH$_2$CH=CH$_2$ | —C$_6$H$_5$ | H | H | 1.5280 | 95 |
| F | —CHCl$_2$ | —CH$_2$CH=CH$_2$ | —CH$_3$ | —(CH$_2$)$_4$— | | 1.4860 | 91 |
| G | —CHCl$_2$ | —CH$_2$CH=CH$_2$ | —C$_2$H$_5$ | —(CH$_2$)$_4$— | | 1.4815 | 91 |
| H | —CHCl$_2$ | —CH$_2$CH=CH$_2$ | —(CH$_2$)$_4$— | | H | 1.4967 | 90 |
| I | —CHBrCH$_2$Br | —CH$_2$CH=CH$_2$ | —CH$_3$ | H | H | 1.5524 | 74 |
| J | —CHBrCH$_2$Br | —CH$_2$CH=CH$_2$ | —C$_2$H$_5$ | H | H | 1.5478 | 80 |
| K | —CHCl$_2$ | —C$_3$H$_7$ | —CH$_3$ | H | H | 1.4710 | 88 |

TABLE 1-continued $$R^1-\overset{\overset{O}{\|}}{C}-N\overset{R^2}{\underset{CH_2-O-CH-CH-O-R^3}{\diagdown}} \quad (III)$$
$$\phantom{R^1-C-N-CH_2-O-CH-}\underset{R^5}{|}\phantom{-}\underset{R^4}{|}$$

| Sign of the compound | R¹ | R² | R³ | R⁴ | R⁵ | $n_D^{25}$ | Yield (%) |
|---|---|---|---|---|---|---|---|
| L | —CHCl₂ | —C₃H₇ | —C₂H₅ | H | H | 1.4631 | 90 |
| M | —CHCl₂ | —C₃H₇ | —CH₃ | H | —CH₃ | 1.4640 | 87 |
| N | —CHCl₂ | —CH₂CH₂CH(CH₃)₂ | —CH₂CH₂OC₂H₅ | H | H | 1.4549 | 93 |
| O | —CHCl₂ | —CH₃ | —CH₃ | H | H | 1.4750 | 75 |
| P | —CHCl₂ | —CH₃ | —C₂H₅ | H | H | 1.4692 | 77 |
| R | —CHCl₂ | —CH₃ | —C₄H₉ | H | H | 1.4640 | 88 |
| S | —CHCl₂ | —CH₃ | —CH₃ | H | —CH₃ | 1.4700 | 75 |
| T | —CHCl₂ | —CH(CH₃)₂ | —CH₃ | H | H | 1.4710 | 87 |
| U | —CHCl₂ | —CH(CH₃)₂ | —C₂H₅ | H | H | 1.4673 | 87 |
| V | —CHCl₂ | —CH(CH₃)₂ | —CH₃ | —CH₃ | H | 1.4679 | 82 |

The acetamide derivatives of the formula (III) of the invention can particularly be useful as antidotes for increasing the selectivity and for reducing the harmful effect on cultivated plants of herbicide compositions containing thiocarbamate derivatives of the formula (I) or chloroacetanilide derivatives of the formula (II) as active ingredients.

The antidotes of the invention can mainly be employed for such active agents of the formula (I), wherein R⁶ and R⁷ stand for an alkyl group of 1 to 4 carbon atoms or a cyclohexyl group; or R⁶ and R⁷ together represent a hexamethylene group; and R⁸ stands for an alkyl group containing 1 to 3 carbon atoms.

Our of the compounds of formula (II), those are preferred wherein

R⁹ and R¹⁰ stand for hydrogen or an alkyl group of 1 or 3 carbon atoms, particularly in positions 2 and 6; and R¹¹ stands for an alkyl group of 1 to 4 carbon atoms or an alkoxyalkyl group containing not more than 4 carbon atoms.

The antidotes of our invention can most preferably be used in order to reduce or prevent the harmful effect on cultivated plants of herbicide compositions containing S-ethyl-N,N-di(n-propyl)thiocarbamate, S-ethyl-N,N-diisobutylthiocarbamate, S-ethyl-N,N-hexamethylenethiocarbamate, S-ethyl-N-cyclohexyl-N-ethylthiocarbamate, S-(n-propyl)-N,N-di (n-propyl)thiocarbamate, S-propyl-N-butyl-N-ethyl-thiocarbamate, 2-methyl-6-ethyl-N-(ethoxymethyl)chloroacetanilide and 2-methyl-6-ethyl-N-(methoxyisopropyl)chloroacetanilide as active ingredient.

The antidotes of our invention and the herbicide compositions containing thiocarbamate derivatives or chloroacetanilide derivatives can be used together, that is, in a mixture, or separately, that is, simultaneously or consecutively; thus, these compositions can be applied to the soil before or after sowing.

In the course of a consecutive employment care should be taken that the herbicide composition applied as first does not exert any harmful effect on the cultivated plants before application of the antidote.

The possibility exists to treat the seeds of the cultivated plants with the antidote; in such cases the treatment by the herbicide composition has to be carried out as usual.

The weight ratio of the antidote to the active agent of the herbicide composition can vary within very wide limits. This ratio depends upon the structure of the antidote and the herbicidally active ingredients, upon the cultivated plant as well as on factors affecting the use of the herbicidally active ingredient and being well known for the person skilled in the art. The weight ratio of the herbicidally active ingredient to the antidote can change from 50:1 to 1:1, for instance 45:1 to 2:1, 40:1 to 3:1, 35:1 to 5:1, 20:1 to 10:1, , suitably 20:1 to 2:1, preferably 20:1, 15:1, 10:1, 5:1 and 4:1.

The amount of the antidote applied is always adjusted to the amount of the herbicide required per one hectare, by considering of the above-mentioned ratios. When applied together, the amount may, in general, be 1 to 20 kg per hectare as calculated for the total of active ingredients. When applied alone, the amount of the composition containing the antidote may be in general 0.02 to 10 kg, suitably 0.1 to 5 kg and preferably 0.1 to 1 kg, as calculated for the active ingredient of the antidote.

It is essential from the point of view of the application that both the herbicide composition and the antidote, together or separately, should be used in such an amount that the weed control be effective without damaging the cultivated plants.

In the compositions of the invention the herbicide ingredient and the antidote are either together in a mixture or separately. Thus, the invention also includes such compositions within its scope which contain the herbicidally active ingredient together with the antidote; as well as to such compositions which contain the antidote alone as biologically active ingredient.

In general, it can be stated that compositions comprising the herbicide together with the antidote can contain materials that are known for the formulation to compositions of herbicidally active ingredients, mainly of thiocarbamate and chloroacetanilide derivatives, compatible with both active ingredients and agriculturally acceptable.

These compositions may contain the herbicide and antidote in the ratio defined above and the total of the active ingredients may vary from 1 to 99% by weight, preferably from 1 to 90% by weight. Of course, these compositions include the highly concentrated compositions as well as compositions which can be prepared from those by dilution and applied directly. However, the total of the active ingredients in the latter ones can be even 0.01% by weight in extreme cases. The compositions prepared by mixing the herbicidally active ingredient with the antidote in a tank or in a sprayer equipment and optionally diluted before use, are also included within the scope of this invention.

The active ingredient content of the composition comprising the antidote alone may be 1 to 99% by weight preferably 1 to 90% by weight.

The composition of the invention may be any of the solid or liquid compositions acceptable in the agricultural practice, the preparation and efficient use of which are made possible by the physical and chemical properties of the active ingredients. The compositions contain the active ingredients together with an agriculturally acceptable solid or liquid carrier as well as with surface-active additives.

The compositions may also contain other additives advantageously influencing the exertion of the effect or making easy their use. Such additives are, for example, the protective colloids, thickening agents, adhesive agents, stabilizers and the like. In addition to the amount of the active ingredients defined above, the compositions of the invention in general contain 1 to 99% by weight of a solid or liquid carrier and 0.1 to 25% by weight of a surfactant. Any of the organic or inorganic, agriculturally acceptable materials of natural or artificial origin can be used as carrier such as clay, natural or artificial silicates, silicic acid, dolomite, kaolin, diatomaceous earth, grist of plant products and the like as solid carriers; water, alcohols, esters, ketones, mineral oil fractions, aromatic, aliphatic or cyclic hydrocarbons, halogenated hydrocarbons, dimethylformamide, dimethylsulfoxide, N-methylpyrroolidone and the like as liquid carriers.

The surfactant may be any emulsifying agent, a dispersing or wetting agent of either ionic and/or non-ionic type. Examples of these additives are the salts of ligninsulfonic acid, phenosulfonic acid and naphthalenesulfonic acid; the polycondensation products of ethylene oxide with fatty alcohols, fatty acids or fatty acid amides; alkyl aryl sulfonates, substituted phenols, such as alkylphenols and arylphenols as well as polyoxyethylated phenols.

Concerning the useful surfactants known sources of the literature, for example the appropriate parts of "Surfactant Science Series", Ed. Marcel Dekker, Inc., New York, can be referred to.

In general, when the active ingredient or ingredients are insoluble in water and water is used as auxiliary material, for example for dilution, then the presence of at least one surface-active additive is necessary.

The solid compositions of the invention may be powders, dusts or granules. The liquid compositions, that is, the compositions applied in a liquid form, can be solutions, emulsifiable concentrates, emulsions, concentrated suspensions, wettable powders or sprayable powders as well as pastes. The concentrated compositions can adequately be diluted. The compositions are made in a known manner.

The application of the compositions, optionally in an adequately diluted form can be accomplished by conventional methods and devices, for example by spraying, atomization, dusting, spreading and the like.

The following Examples illustrate the ingredients and preparation of some representatives of the compositions of the invention, comprising the herbicide and antidote, without any limitation of the invention.

Example 5

Preparation of a concentrate 93 parts by weight of S-ethyl-N,N-di(n-propyl)thiocarbamate are mixed with 2 parts by weight of N-allyl-N-(2-methoxyethoxymethyl)dichloroacetamide and with 5 parts by weight of Tween 60 (oxyethylated anhydrosorbitol monostearate; HLB=14.9). Thus, a concentrate containing 95% by weight of total active ingredients is obtained which contains the herbicide to the antidote in a 46.5:1 weight ratio.

This concentrate is easy to store and to transport. Before use it is diluted with an organic solvent such as xylene and water and can be applied as a stable, sprayable emulsion.

Example 6

Preparation of an emulsifiable concentrate 10 parts by weight of 2-methyl-6-ethyl-N-(ethoxymethyl)chloroacetanilide are dissolved in 25 parts by weight of xylene and 2.5 parts by weight of N-allyl-N-(2-ethoxyethoxymethyl)dichloroacetamide and then 2 parts by weight of polyoxyethylene fatty acid ester are added. The total active ingredient content of this composition is 31.7% by weight; the weight ratio of the herbicidally active ingredient to the antidote is 4:1.

The concentrate thus obtained can be diluted by water to a stable emulsion of the desired concentration before use, which can be applied by spraying.

Example 7

Preparation of a wettable powder

A mixture of 10 parts by weight of S-ethyl-N,N-di(n-propyl)thiocarbamate, 1 part by weight of N-allyl-N-(2-methoxyethoxymethyl)1,2-dibromopropionic acid amide, 1 part by weight of cetyl polyglycol ether and 88 parts by weight of kaolin is ground in a ball mill. The wettable powder obtained contains 11% by weight of active ingredients and the weight ratio of the herbicidally active ingredient to the antidote os 10:1.

This wettable powder can be suspended in an appropriate volume of water and applied by spraying.

Example 8

Preparation of an emulsifiable concentrate

A mixture is prepared from 70 parts by weight of S-ethyl-N,N-di(n-propyl)thiocarbamate, 3.5 parts by weight of N-(butoxyethoxymethyl)n-allyldichloroacetamide and 3.5 parts by weight of N-(methoxyethoxymethyl)N-allyldicholoroacetamide and this mixture is dissolved in the mixture containing 18 parts by weight of kerosene and 15 parts by weight of an emulsifying agent (a mixture of calcium dodecylbenzenessulfonate with ethylated alkylphenols). The total active ingredient content of this composition is 77% by weight, the weight ratio of the herbicidally active ingredient to the antdote is 10:1. Before use, this composition is diluted by water and then sprayed onto the surface to be treated.

Example 9

Preparation of an emulsifiable concentrate

A mixture containing 35 parts by weight of S-ethyl-N,N-di(n-propyl)thiocarbamate, 35 parts by weight of S-ethyl-N,N-diisobutylthiocarbamate and 7 parts by weight of N-(ethoxyethoxymethyl)-N-allyldichloroacetamide is dissolved in 5 parts by weight of between 60 and 28 parts by weight of xylene. The emulsifiable concentrate thus obtained results in a stable emulsion on dilution with the desired volume of water and this emulsion can be sprayed onto the surface to be treated.

Example 10

Preparation of granules 10 parts by weight of the antidote N-(butoxyethoxymethyl)-N-allyldichloroacetamide are mixed with 2.5 parts by weight of epichlorohydrin, the mixture is dissolved in 70 parts by weight of acetone and 2.5 parts by weight cetyl polyglycol ether and 35 parts by weight of polyethylene glycol are added. The obtained solution is sprayed to 950 parts by weight by kaolin (grain size 0.5 to 0.9 mm), then the acetone is evaporated under reduced pressure. The obtained granules containing 1% by weight of antidote can be sprayed onto the soil surface to be treated.

Example 11

Preparation of a concentrate 95 parts by weight of the antidote N-(ethoxyethoxymethyl)-N-allyldichloroacetamide is mixed with 5 parts by weight of the emulsifying agent Tween 60 to give a concentrate containing 95% by weight of antidote. This composition can be employed similarly to the concentrate described in Example 5.

Example 12

Preparation of an emulsifiable concentrate 50 parts by weight of the antidote N-(methoxyethoxymethyl)-N-propyldichloroacetamide are dissolved in the mixture of 5 parts by weight of polyoxyethylene fatty acid ester and 45 parts by weight of xylene. The obtained emulsifiable concentrate, which contains 50% by weight of antidote, can be diluted by water to a stable emulsion before use ad sprayed onto the soil surface to be treated.

By using similar methods to those described in the above Examples, an appropriate composition can be prepared of any of the antidotes listed in Table 1, and optionally by employing a thiocarbamate or chloroacetanilide derivative. A composition can also be made comprising the antidote alone in an admixture with the appropriate additives.

The simultaneous biological effects of the herbicide compositions comprising the antidotes of the invention and a thiocarbamate derivative or a chloroacetanilide derivative as active ingredient were studied in the greenhouse and in the field.

These investigations were accomplished with the following plants: maize (*Zea mays*), barley (*Hordeum vulgare*), wild oat (*Avena fatua*), barnyard grass (*Echinochloa crus-galli*), mustard (*Sinapis album*), goose-goot (*Chenopodium spp.*), millet (*Setaria glauca*), pea (*Pisum sativum*) and sugar beet (*Beta vulgaris*).

It was stated on the basis of our experiments that the compositions of this invention effectively control the particularly harmful monocotyledonous weeds, mainly barnyard grass, wild oat and millet without damaging the cultivated plants, mainly maize and eventually pea and sugar beet; thus, the herbicide compositions became selective by the use of antidotes. The protective action of the antidotes of the invention was at least identical to that of N,N-diallyldichloroacetamide, a known antidote and eventually, the antidotes of this invention proved to be much more effective.

GREENHOUSE TESTS

Example I

A mixture containing sterile sand and vegetable soil in an 1:2 ratio by weight was placed in plastic dishes of 30×30×15 cm dimension in amounts to give a 10 cm soil thickness after wetting.

The dry soil was mixed slowly, under continuous stirring with 100 ml of an aqueous emulsion of the composition containing the mixture of the herbicide with the antidote, and a predetermined amount of 2 liters were taken out. The soil remaining in the dish was compacted, 10×10 holes with an 1 cm depth were made on the surface by means of a planting template, the maize grains were placed in these holes and covered by the soil taken out previously. The thickness of the covering layer was about 2 cm. The first sprinkling was made by 500 ml of water and subsequently, 100 ml of water were daily added to each cultivating dish. The emulsifiable composition used for this test is prepared analogously to Example 6. 1.23 g. of S-ethyl-N,N-di(n-propyl) thiocarbamate (EPTC) are mixed with 0.12 g. of the antidote, 0.1 g. of an emulsifying agent containing 0.1 g. of polyoxyethylene fatty acid ester and 3.1 g. (3.6 ml.) of xylene and then this mixture is emulsified in 1 liter of water. 100 ml of the thus obtained emulsion is equal to an EPTC plus antidote mixture of a 10:1 weight ratio, that is, to an amount of 10 kg/hectare in the dish with the surface given. This amount is the twofold of that employed in the practice.

The result was evaluated at the end of the 2nd and 3rd week. The deformed stems were counted, the average height and the average green weight of each 25 plants were measured. These results are summarized in Table 2.

TABLE 2

| Antidote | Deformation (%) | The experimental plant | | Green weight (g.) 3rd week |
|---|---|---|---|---|
| | | Height (cm.) | | |
| | | 2nd week | 3rd week | |
| N,N—diallyl-dichloroacet-amide (known) | 0 | 25.1 | 46.5 | 83 |
| A | 0 | 25.2 | 44.8 | 82 |
| B | 0 | 24.1 | 44.5 | 74 |
| C | 0 | 25.0 | 44.1 | 64 |
| D | 0 | 25.6 | 47.4 | 79 |
| E | 0 | 26.0 | 44.9 | 74 |
| F | 1 | 25.6 | 45.6 | 80 |
| G | 0 | 25.1 | 47.1 | 74 |
| H | 0 | 25.0 | 46.1 | 73 |
| I | 0 | 25.5 | 45.5 | 71 |
| J | 1 | 24.9 | 45.9 | 75 |
| K | 0 | 25.3 | 46.5 | 79 |
| L | 0 | 25.2 | 44.6 | 84 |
| M | 0 | 25.4 | 46.6 | 82 |
| N | 1 | 25.4 | 45.2 | 75 |
| O | 0 | 25.6 | 46.1 | 81 |
| P | 0 | 25.4 | 47.0 | 78 |
| R | 0 | 25.2 | 46.6 | 72 |
| S | 1 | 25.1 | 46.4 | 83 |
| T | 1 | 25.4 | 45.5 | 80 |
| U | 0 | 25.3 | 46.9 | 73 |
| V | 0 | 24.2 | 46.4 | 75 |
| without antidote | 9 | 20.7 | 35.7 | 56 |
| untreated control | 0 | 25.4 | 46.6 | 79 |

It can be seen from the data of Table 2 that the protective ingredients of the invention, similarly to the known antidotes, effectively protected the maize from the damage caused by EPTC, and eventually had a stronger effect.

Example II

The procedure of Example I was followed, except that the seeds of plants indicated in Table 3 were sown in 9 rows per dish. From maize 20, from the other plants 50 seeds were sown in one row.

The emulsifiable composition was used in this test is prepared as follows:

0.338 g. of 2-methyl-6-ethyl-N-(ethoxymethyl)-chloroacetanilide, 0.4 ml of xylene, 0.084 g. of the antidote and 0.05 g. of the polyoxyethylene fatty acid ester emulsifying agent are mixed and this mixture is emulsified in 1 liter of water. 100 ml. of the thus obtained emulsion is equal to 2.5 kg/hectare of the herbicidally active ingredient in the dish with the surface given.

The weight ratio of the herbicide to the antidote is 4:1 which is the correct amount to be used in the practice.

The results were evaluated at the end of the third week following the sowing.

The average height (cm.) was measured and the relative condition of the plants was estimated (control=100%).

TABLE 4

| EPTC plus antidote (kg./ha.) | Emerged from 100 seeds (pieces) | Perished (%) | Relative weight of the green mass (%) |
|---|---|---|---|
| 10 + 10 | 97 | 0 | 92 |
| 10 + 5 | 98 | 0 | 95 |
| 10 + 2 | 97 | 0 | 98 |
| 10 + 1 | 95 | 0 | 100 |
| 10 + 0.5 | 97 | 0 | 97 |
| 10 + 0.25 | 97 | 0 | 95 |
| 10 + 0 | 96 | 90 | 11 |
| untreated control | 98 | 0 | 100 |

It is clearly seen from the data of Table 4 that the antidote A, used even at the lowest concentration, that is in a 40:1 ratio of EPTC to the antidote, effectively protects the maize against the damaging effect of the herbicidally active ingredient.

Subsequently, the protective action of the antidotes of the invention was studied in the cases of herbicide compositions containing practically important thiocarbamate derivatives as active ingredients.

Example IV

Dishes of 30×30×19 cm. were filled with quartz sand to a depth of 8 cm. and 100 maize seeds were sown into each dish. Before emergence, the sand was sprayed

TABLE 3

| Plants | Untreated control | | Active ingredient | | Active ingredient plus antidote | | | | | | | | | | | |
|---|---|---|---|---|---|---|---|---|---|---|---|---|---|---|---|---|
| | | | | | A | | B | | C | | D | | E | | F | |
| | AH | RC | AH | RC | AH | AR | AH | RC | AH | RC | AH | RC | AH | RC | AH | RC |
| Maize | 50 | 100 | 29 | 70 | 35 | 70 | 42 | 100 | 45 | 100 | 40 | 90 | 35 | 80 | 35 | 70 |
| Barley | 40 | 100 | 8 | 10 | 6 | 10 | killed | | 6 | 10 | 8 | 20 | 4 | 15 | 4 | 20 |
| Wild-oat | 30 | 100 | killed | | killed | | killed | | killed | | killed | | 2 | 10 | 3 | 15 |
| Barnyard grass | 11 | 100 | killed | | killed | | killed | | killed | | killed | | killed | | killed | |
| Mustard | 13 | 100 | 5 | 15 | 5 | 10 | 4 | 10 | 6 | 20 | 5 | 10 | 8 | 20 | 6 | 20 |
| Goose-foot | 3 | 100 | killed | | killed | | killed | | killed | | killed | | killed | | killed | |
| Millet grass | 11 | 100 | killed | | killed | | killed | | killed | | killed | | killed | | killed | |
| Pea | 9 | 100 | 7 | 10 | 6 | 30 | 6 | 30 | 10 | 80 | 11 | 110 | 6 | 40 | 9 | 80 |
| Sugar beet | 9 | 100 | 3 | 10 | 4 | 20 | 4 | 60 | 6 | 25 | 7 | 75 | 7 | 90 | 6 | 70 |

AH = Average Height (cm.)
RC = Relative Condition (estimated value, %)
Active ingredient: 2-Methyl-6-ethyl-N—(ethoxymethyl)chloroacetanilide It is obvious from the data of Table 3 that the antidotes, while maintaining the herbicidal activity, protect the maize from the damage caused by 2-methyl-6-ethyl-N-(ethoxymethyl)chloroacetanilide. An important protective action is observed at the antidote C for the maize, at antidote D for the pea and at antidote E for the sugar beet. When applied alone, the herbicidally active ingredient strongly damages the maize, pea and sugar beet, respectively.

Example III

Dishes of 30×30×15 cm. were filled with quartz sand to a depth of 8 cm. and 100 maize seeds were sown into the sand. Before emergence, the sand was sprayed by an emulsion made with 1 liter of water from the emulsifiable concentrate prepared analogously to Example 6 from the mixture of 10 kg. of EPTC and of an amount of antidote A required to 10, 5, 1, 0.5 and 0.25 kg/hectare, respectively. After spraying, an additional sand layer of 2 cm was sprayed onto the surface. The results were evaluated at the end of the 6th week and are summarized in Table 4.

by the emulsion made with 1 liter of water from the emulsifiable concentrate prepared from the mixture of 10 kg. of a thiocarbamate active ingredient and 1 kg. of the antidote (antidotes A, B or N,N-diallyldichloroacetamide). In our case, 0.228 g. of the thiocarbamate was used with 0.03 g. of the antidote. After spraying, an additional sand layer of 2 cm. was sprayed onto the surface. The results were evaluated at the end of the 4th week and are summarized in Table 5.

TABLE 5

| Active ingredient plus antidote | Number of maize plants | |
|---|---|---|
| | emerged (pieces) | deformed (pieces) |
| EPTC + A | 96 | 0 |
| EPTC + B | 97 | 1 |
| EPTC + X (known) | 97 | 1 |
| EPTC | 95 | 47 |
| butylate + A | 93 | 4 |
| butylate + B | 94 | 2 |
| butylate + X (known) | 97 | 2 |
| butylate | 98 | 3 |
| molinate + A | 100 | 8 |
| molinate + B | 95 | 9 |
| molinate + X (known) | 97 | 14 |
| molinate | 96 | 56 |
| cycloate + A | 95 | 6 |

TABLE 5-continued

| Active ingredient plus antidote | Number of maize plants | |
|---|---|---|
| | emerged (pieces) | deformed (pieces) |
| cycloate + B | 97 | 4 |
| cycloate + X (known) | 98 | 10 |
| cycloate | 95 | 31 |
| vernolate + A | 100 | 9 |
| vernolate + B | 98 | 4 |
| vernolate + X (known) | 98 | 9 |
| vernolate | 95 | 25 |
| A | 96 | 0 |
| B | 97 | 0 |
| X (known) | 97 | 0 |

EPTC = S—ethyl-N,N—di(n-propyl)thiocarbamate
butylate = S—ethyl-N—N—diisobutylthiocarbamate
molinate = S—ethyl-N,N—hexamethylenethiocarbamate
cycloate = S—ethyl-N,N—cyclohexyl-N—ethylthiocarbamate
vernolate = S—(n-propyl) N,N—di(n-propyl)thiocarbamate
X = N,N—diallyldichloroacetamide It is obvious from the data of Table 5 that, on the use of the herbicides S-ethyl-N,N-di(n-propyl)thiocarbamate mate (EPTC) and S-ethyl-N,N-diisobutylthiocarbamate (butylate), the protective action of both antidote A and antidote B is practically identical with that of the known N,N-diallyldichloroacetamide (compound X), while the protective action of the antidote A and antidote B is stronger than that of compound X when S-ethyl-N,N-hexamethylenethiocarbamate (molinate), S-ethyl-N-cyclohexyl-N-ethylthiocarbamate (cycloate) or S-(n-propyl)-N,N-di(n-propyl)thiocarbamate (vernolate) are used as herbicidally active ingredients.

FIELD EXPERIMENTS

Example V

In the course of a small-lot field experiment, before the sowing of maize, the aqueous emulsion (prepared as in Example II) from an emulsifiable concentrate containing a mixture of 10 kg. of EPTC (as calculated uniformly for one hectare) together with various amounts of the antidote B of the invention was sprayed out and harrowed into the soil to a depth of about 4 cm. Then, the maize was sown. As a control, EPTC was applied without any antidote and in an admixture with N,N-diallyldichloroacetamide, respectively. The results obtained are summarized in Table 6.

TABLE 6

| Antidote | Weight ratio of antidote to EPTC | Number of deformed maize plants (pieces/12.5 π) series | | | |
|---|---|---|---|---|---|
| | | I | II | III | IV |
| | EPTC alone | 67 | 37 | 41 | 45 |
| X (known) | 1:12.0 | 0 | 1 | 2 | 1 |
| B | 1:12.0 | 0 | 1 | 0 | 2 |
| B | 1:3.6 | 0 | 1 | 1 | 1 |

Antidote B = N—allyl-N—(2-ethoxyethoxymethyl)dichloroacetamide
The amount (dosis) of EPTC is uniformly 10 kg./hectare
X = N,N—diallyldichloroacetamide It can be seen from the experiment data that, within the limits of the experimental errors, the antidote of the invention under field conditions possesses a protective action at least identical to that of N,N-diallyldichloroacetamide used as control. EPTC causes severe damage to the maize plant when no antidote is employed.

We claim:

1. A compound of the Formula (III)

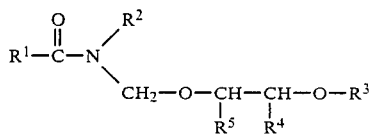

wherein $R^1$ stands for a halogenated alkyl group containing 1 to 2 carbon atoms;

$R^2$ stands for a straight or branched alkyl group containing 1 to 6 carbon atoms or an alkenyl group containing 2 to 6 carbon atoms;

$R^3$ stands for an alkyl group containing 1 to 6 carbon atoms, an alkoxyalkyl group of altogether 2 to 6 carbon atoms, or a phenyl group; or $R^3$ and $R^4$ together stand for a propylene group or a butylene group; or $R^4$ and $R^5$ stand independently from each other for hydrogen or a methyl group; or $R^4$ and $R^5$ together stand for a propylene group or a butylene group.

2. A compound of the Formula (III)

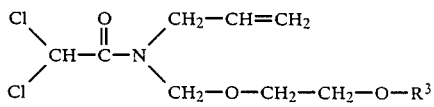

wherein $R^3$ stands for an alkyl group containing 1 to 6 carbon atoms, an alkoxyalkyl group of altogether 2 to 6 carbon atoms, or a phenyl group.

3. The compound of the Formula (III) defined in claim 2 which is

N-allyl-N-(2-methoxyethoxymethyl)-dichloroacetamide;

N-allyl-N-(2-ethoxyethoxymethyl)-dichloroacetamide; or

N-allyl-N-(2-phenoxyethoxymethyl)-dichloroacetamide.

4. An antidote composition comprising as active ingredient 1 to 99% by weight of the compound of the Formula (III) as defined in claim 1.

5. An antidote containing herbicide composition, which comprises as an antidote, at least one compound of the Formula (III) as defined in claim 1, and as an herbicide at least one thiolcarbamate of the Formula (I)

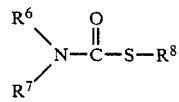

or chloroacetanilide of the Formula (II)

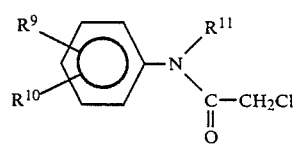

wherein

R⁶ and R⁷ each stand for an alkyl group of 1 to 4 carbon atoms, or a cyclohexyl group; or R⁶ and R⁷ together form a hexamethylene group;

R⁸ stands for an alkyl group of 1 to 3 carbon atoms;

R⁹ and R¹⁰ stand for hydrogen, or an alkyl group of 1 to 3 carbon atoms; and

R¹¹ stands for an alkyl group of 1 to 4 carbon atoms, or an alkoxyalkyl group of altogether 2 to 4 carbon atoms; and the ratio of the herbicide to the antidote is 50:1 to 1:1.

6. The antidote-containing herbicide composition defined in claim 5 which comprises as an antidote a compound of the Formula (III) selected from the group consisting of N-allyl-N-(2-methoxyethoxymethyl)-dichloroacetamide, N-allyl-N-(2-ethoxyethoxymethyl)-dichloroacetamide, and N-allyl-N-(2-phenoxyethoxymethyl)-dichloroacetamide;

and as an herbicide of the Formula (I) the compound EPTC.

7. The antidote-containing herbicide composition defined in claim 5 which comprises as an antidote a compound of the Formula (III) selected from the group consisting of N-allyl-N-(2-methoxyethoxymethyl)-dichloroacetamide, N-allyl-N-(2-ethoxyethoxymethyl)-dichloroacetamide, and N-allyl-N-(2-phenoxyethoxymethyl)-dichloroacetamide;

and as an herbicide of the Formula (II) the compound acetochlor.

8. A method of cultivating crop plants at a plant site which comprises applying to said site an amount of a herbicide effective to kill weeds, in the presense of an antidote—in an amount effective to protect the crop plants, said antidote consisting of at least one acetamide of the Formula (III)

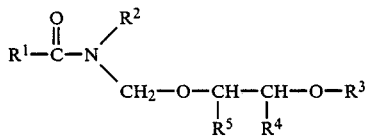

wherein R¹ stands for a halogenated alkyl group containing 1 to 2 carbon atoms;

R² stands for a straight or branched alkyl group containing 1 to 6 carbon atoms or an alkenyl group containing 2 to 6 carbon atoms, R³ stands for an alkyl group containing 1 to 6 carbon atoms, an alkoxyalkyl group of altogether 2 to 6 carbon atoms, or a phenyl group, or R³ and R⁴ together stand for a propylene group or a butylene group, or R⁴ and R⁵ stand independently from each other for hydrogen or a methyl group, or R⁴ and R⁵ together stand for a propylene group or a butylene group; and said herbicide being at least one thiobamate of the Formula (I)

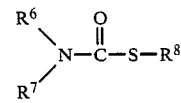

or chloroacetanilide of the Formula (II)

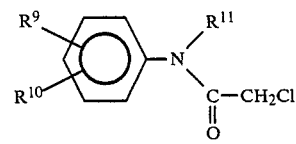

wherein R⁶ and R⁷ stand for an alkyl group of 1 to 4 carbon atoms, or a cyclohexyl group, or R⁶ and R⁷ together form a hexamethylene group, R⁸ stands for an alkyl group of 1 to 3 carbon atoms, R⁹ and R¹⁰ stand for hydrogen or an alkyl group of 1 to 3 carbon atoms, R¹¹ stands for an alkyl group of 1 to 4 carbon atoms or an alkoxyalkyl group of altogether 2 to 4 carbon atoms, and the ratio of the herbicide to the antidote is 50:1 to 1:1.

9. The method of cultivating a plant or crop as defined in claim 8 wherein the compound of the Formula (I) is selected from the group consisting of N-allyl-N-(2-methoxyethoxymethyl)-dichloroacetamide, N-allyl-N-(2-ethoxyethoxymethyl)-dichloroacetamide, and N-allyl-N-(2-phenoxyethoxymethyl)-dichloroacetamide;

and the herbicide of the Formula (II) is EPTC.

10. The method of cultivating a plant crop as defined in claim 8 wherein the compound of the Formula (I) is selected from the group consisting of N-allyl-N-(2-methoxyethoxymethyl)-dichloroacetamide, N-allyl-N-(2-ethoxyethoxymethyl)-dichloroacetamide, and N-allyl-N-(2phenoxyethoxymethyl)-dichloroacetamide;

and the herbicide of the Formula (III) is acetochlor.

* * * * *